United States Patent [19]
Shimada et al.

[11] Patent Number: 5,233,090
[45] Date of Patent: Aug. 3, 1993

[54] [2,2]PARACYCLOPHANE COMPOUNDS FOR USE IN ELECTROPHOTOGRAPHIC PHOTOCONDUCTORS

[75] Inventors: Tomoyuki Shimada, Numazu; Masaomi Sasaki, Susono; Tamotsu Aruga, Mishima, all of Japan

[73] Assignee: Ricoh Company, Ltd., Tokyo, Japan

[21] Appl. No.: 788,438

[22] Filed: Nov. 6, 1991

Related U.S. Application Data

[63] Continuation-in-part of Ser. No. 429,482, Oct. 31, 1989, Pat. No. 5,098,807.

[30] Foreign Application Priority Data

Nov. 11, 1988 [JP] Japan .................. 63-284928
Nov. 11, 1988 [JP] Japan .................. 63-284929

[51] Int. Cl.$^5$ .................................. C07C 211/61
[52] U.S. Cl. ............................. 564/426; 564/308
[58] Field of Search ....................... 564/426, 308

[56] References Cited

U.S. PATENT DOCUMENTS 3,945,823 3/1976 Parent et al. .................. 96/1 SD

OTHER PUBLICATIONS

DeWhirst et al, JACS, vol. 80 (1958) pp. 3115-3125.

Primary Examiner—Richard L. Raymond
Attorney, Agent, or Firm—Oblon, Spivak, McClelland, Maier & Neustadt

[57] ABSTRACT

[2,2]paracyclophane compounds having formula (I):

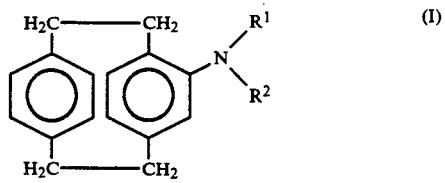

wherein $R^1$ and $R^2$ independently represent an alkyl group having 1 to 4 carbon atoms, which may have a substituent, or an aryl group which may have a substituent, provided that $R^1$ and $R^2$ may not be a methyl group at the same time, and methods of producing the same are disclosed. These compounds are useful as an effective photoconductive component for an electrophotographic photoconductor which is composed of an electroconductive support and a photoconductive layer formed thereon.

16 Claims, 4 Drawing Sheets

[2,2]PARACYCLOPHANE COMPOUNDS FOR USE IN ELECTROPHOTOGRAPHIC PHOTOCONDUCTORS

This application is a continuation-in-part of application Ser. No. 07/429,482, filed Oct. 31, 1989, now U.S. Pat. No. 5,098,807.

BACKGROUND OF THE INVENTION

1. Field of the Invention

The present invention relates to [2,2]paracyclophane compounds which can be used as photoconductive materials in electrophotographic photoconductors comprising an electroconductive support and a photoconductive layer comprising a photoconductive material, and methods of producing the [2,2]paracyclophane compounds.

2. Discussion of Background

Conventionally, inorganic materials such as selenium, cadmium sulfide and zinc oxide are used as photoconductive materials of an electrophotographic photoconductor in the electrophotographic process. The above-mentioned electrophotographic process is one of the image forming processes, through which the surface of the photoconductor is charged uniformly in the dark to a predetermined polarity, for instance, by corona charge. The uniformly charged photoconductor is exposed to a light image to selectively dissipate the electrical charge of the exposed areas, so that a latent electrostatic image is formed on the photoconductor. The thus formed latent electrostatic image is developed by a developer comprising a coloring agent such as a dye and a pigment, and a binder agent such as a polymeric material, to a visible image.

Fundamental characteristics required for the photoconductor in such an electrophotographic process are: (1) chargeability to an appropriate potential in the dark, (2) minimum dissipation of electrical charge in the dark, and (3) rapid dissipation of electrical charge when exposed to the light.

However, while the above-mentioned inorganic materials have many advantages, they have several shortcomings form the viewpoint of practical use.

For instance, a selenium photoconductor, which is widely used at present, satisfies the above-mentioned requirements (1) to (3) completely, but it has the shortcomings that its manufacturing conditions are difficult, and accordingly its production cost is high. In addition, it is difficult to work it into the form of a belt due to its poor flexibility, and it is so vulnerable to heat and mechanical shocks that it must be handled with the utmost care.

A cadmium sulfide photoconductor and a zinc oxide photoconductor can be easily obtained by coating a dispersion of cadmium sulfide particles and zinc oxide particles in a binder resin on a support. However, they are poor in mechanical properties, such as surface smoothness, hardness, tensile strength and wear resistance. Therefore, they cannot be used in the repeated operation, as they are.

To solve the above-mentioned problems of the inorganic materials, various electrophotographic photoconductors employing organic materials are proposed recently and some are still put to practical use. For example, there are known a photoconductor comprising poly-N-vinylcarbazole and 2,4,7-trinitrofluorene-9-on, as disclosed in U.S. Pat. No. 3,484,237; a photoconductor prepared by sensitizing poly-N-vinylcarbazole with a pigment of pyrylium salt, as described in Japanese Patent Publication 48-25658; a photoconductor comprising as the main component an organic pigment, as described in Japanese Laid-Open Patent Application 47-37543; a photoconductor comprising as the main component an eutectic crystal complex of a dye and a resin, as described in Japanese Laid-Open Patent Application 47-10735; a photoconductor prepared by sensitizing a triphenylamine compound with a sensitizer pigment, as described in U.S. Pat. No. 3,180,730; and a photoconductor comprising poly-N-vinylcarbazole and an amine derivative as a charge transporting material, as described in Japanese Laid-Open Patent Application 58-1155.

These electrophotographic photoconductors have their own excellent characteristics and considered to be valuable for practical use. With various requirements of the electrophotographic photoconductor in electrophotography taken into consideration, however, the above-mentioned conventional electrophotographic photoconductors cannot meet all the requirements.

In U.S. Pat. No. 3,265,496, Japanese Patent Publication 39-11546 and Japanese Laid-Open Patent Application 53-27033, polyfunctional tertiary amine compounds, in particular benzidine compounds among them, are considered to be excellent as photoconductive materials for use in the electrophotographic photoconductor. However, these compounds have the shortcomings that the solubility in a binder resin is poor and they are easily crystallized in a photoconductive layer. To remove the above shortcomings, it is proposed in Japanese Laid-Open Patent Application 62-112164 that the above benzidine compound be used together with other low-molecular weight compounds in the photoconductive layer to minimize the crystallization of the benzidine compound.

Furthermore, 4-N,N-dimethylamino[2,2]paracyclophane is conventionally known as a [2,2]paracyclophane compound containing a tertiary amino group as reported in J. Am. Chem. Soc., 80, p.3115(1958), but it does not sufficiently function as a photoconductive material.

SUMMARY OF THE INVENTION

It is therefore a first object of the present invention to provide novel [2,2]paracyclophane compounds used as photoconductive materials in an electrophotographic photoconductor having good durability, free from the conventional shortcomings, which can completely satisfy all the requirements in the electrophtographic process, can be easily manufactured at relatively low cost.

A second object of the present invention is to provide a method of producing the above [2,2]paracyclophane compounds.

The first object of the present invention can be achieved by a [2,2]paracyclophane compound having formula (I):

wherein $R^1$ and $R^2$ each represent an alkyl group having 1 to 4 carbon atoms, which may have a substituent, or an aryl group, which may have a substituent, and $R^1$ and $R^2$ may be the same or different, provided that both $R^1$ and $R^2$ cannot be a methyl group at the same time.

The second object of the present invention is attained by allowing 4-amino[2,2]paracyclophane compound having formula (II) to react with a halide of formula (III), as shown in the following reaction scheme:

wherein $R^1$ and $R^2$ are the same as those defined in the above formula (I); and X represent halogen.

Alternatively, the second object of the present invention is attained by allowing a halogenated [2,2]paracyclophane of formula (IV) to react with an amino compound of formula (V), as shown in the following reaction scheme:

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DETAILED DESCRIPTION OF THE PREFERRED EMBODIMENTS

According to the present invention, an electrophotographic photoconductor comprising an electroconductive support and a photoconductive layer formed thereon, which photoconductive layer comprises at least one [2,2]paracyclophane compound of formula (I) can be provided.

wherein $R^1$ and $R^2$ independently represent (i) an alkyl group having 1 to 4 carbon atoms, which may have a substituent, or (ii) an aryl group which may have a substituent, provided that $R^1$ and $R^2$ may not be a methyl group at the same time.

Preferable examples of the above-mentioned [2,2]-paracyclophane compounds of formula (I) are as follows:

(1) the [2,2]paracyclophane compounds of formula (I) in which the substituent of the alkyl group represented by $R^1$ or $R^2$ is a phenyl group or an alkylphenyl group; and the aryl group represented by $R^1$ or $R^2$ is selected from the group consisting of a phenyl group, a biphenyl group and a phenoxyphenyl group, which may be substituted by an alkyl group having 1 to 4 carbon atoms, an alkoxyl group having 1 to 4 carbon atoms, or a dialkylamino group.

(2) the [2,2]paracyclophane compounds of formula (I) in which at least one of $R^1$ or $R^2$ is the above-defined aryl group;

(3) the [2,2]paracyclophane compounds of formula (I) in the substituents of $R^1$ and $R^2$ are identical;

(4) the [2,2]paracyclophane compounds of formula (I) in $R^1$ and $R^2$ are a phenyl group which may have a substituent selected from the class of an alkyl group having 1 to 4 carbon atoms, and an alkoxyl group having 1 to 4 carbon atoms;

(5) the [2,2]paracyclophane compounds of formula (I) in the substituents of R¹ and R² are identical, and an ethyl group or a phenyl group;

(6) the [2,2]paracyclophane compounds of formula (I) in R¹ and R² are a phenyl group which may be substituted by a methyl group or a methoxy group; and (7) the [2,2]paracyclophane compounds of formula (I) in R¹ and R² are a phenyl group.

Specific examples of the above-mentioned [2,2]paracyclophane compounds of formula (I) are as follows:

TABLE 1

| Compound No. | R¹ | R² |
|---|---|---|
| 1 | CH₃ | CH₃ |
| 2 | CH₃ | C₂H₅ |
| 3 | C₂H₅ | C₂H₅ |
| 4 | C₃H₇ | C₃H₇ |
| 5 | CH₃ | —CH₂—⌬ |
| 6 | CH₃ | —⌬ |
| 7 | —CH₂—⌬ | —CH₂—⌬ |
| 8 | —CH₂—⌬—CH₃ | —CH₂—⌬ |
| 9 | —⌬ | —CH₂—⌬ |
| 10 | —⌬ | —⌬—CH₃ |
| 11 | —⌬(CH₃) | —⌬(CH₃) |
| 12 | —⌬(H₃C) | —⌬(H₃C) |
| 13 | —⌬ | —⌬(CH₃) |
| 14 | —⌬ | —⌬(H₃C) |
| 15 | —⌬—C₂H₅ | —⌬—C₂H₅ |
| 16 | —⌬—tC₄H₉ | —⌬—tC₄H₉ |
| 17 | —⌬ | —⌬—OCH₃ |

TABLE 1-continued

| Compound No. | R¹ | R² |
|---|---|---|
| 18 | —⌬—OCH₃ | —⌬—OCH₃ |
| 19 | —⌬(OCH₃) | —⌬(OCH₃) |
| 20 | —⌬(H₃CO) | —⌬(H₃CO) |
| 21 | —⌬ | —⌬—OC₂H₅ |
| 22 | —⌬—CH₂ | —⌬—OCH₃ |
| 23 | —⌬—⌬ | —⌬—CH₂ |
| 24 | —⌬—⌬ | —⌬—⌬ |
| 25 | —⌬—⌬—CH₃ | —⌬—⌬—CH₃ |
| 26 | —⌬—⌬—C₂H₅ | —⌬—⌬—C₂H₅ |
| 27 | —⌬—⌬—OCH₃ | —⌬—⌬—OCH₃ |
| 28 | —⌬—⌬—tC₄H₉ | —⌬—⌬—tC₄H₉ |
| 29 | —⌬—N(CH₃)₂ | —⌬ |
| 30 | —⌬—N(C₂H₅)₂ | —⌬—N(C₂H₅)₂ |
| 31 | —⌬—O—⌬ | —⌬—O—⌬ |

The [2,2]paracyclophane compounds of formula (I) can be obtained by allowing 4-amino[2,2]paracyclophane compound having formula (II) to react with a halide of formula (III), as shown in the following reaction scheme:

wherein R¹ and, R² are the same as those defined in the formula (I); and X represents a halogen.

Alternatively, the above-mentioned [2,2]paracyclophane compounds of formula (I) can be obtained by allowing a halogenated [2,2]paracyclophane compound of formula (IV) to react with an amino compound of formula (V), as shown in the following reaction scheme:

wherein R¹ and, R² are the same as those defined in the formula (I); and X represents a halogen.

More specifically, [2,2]paracyclophane compounds of formula (I) according to the present invention can be obtained by allowing 4-amino[2,2]paracyclophane of formula (II) to react with a halide of formula (III), or allowing halogenated [2,2]paracyclophane of formula (IV) to react with an amine compound of formula (V) in a solvent at room temperature to about 100° C., in the presence of a basic catalyst. The above reactions can also be carried out at temperatures of about 150° to 250° C. in a stream of nitrogen, in a solvent or without any solvent, with the addition thereto of a copper powder, copper oxide or copper halogenide, and an alkaline salt or an alkaline material in a sufficient amount to neutralize hydrogen halogenide generated in the course of condensation reaction.

In the case where the above reaction is carried out in a solvent in the presence of a basic catalyst, sodium hydroxide, sodium amide and sodium bicarbonate can be used as the basic catalyst. Examples of the reaction solvents employed in this reaction are dioxane, tetrahydrofuran, toluene, xylene, N,N-dimethylformamide, ethanol and methanol.

When the reaction is carried out using an alkaline salt or an alkaline material to the reaction mixture, alkaline materials such as sodium hydroxide and potassium hydroxide and alkaline salts such as sodium carbonate and potassium carbonate can be employed. Examples of the reaction solvents employed in this reaction are nitrobenzene, dichlorobenzene, quinoline, N, N-dimethylformamide, dimethyl sulfoxide, N-methylpyrrolidone, and 1,3-dimethyl-2-imidazolidinone.

The above-mentioned [2,2]paracyclophane compounds for use in the present invention, which are remarkably effective as photoconductive materials in the electrophotographic photoconductor, are optically or chemically sensitized with a sensitizer such as a dye or Lewis acid. In addition, the [2,2]paracyclophane compounds effectively function as charge transporting materials in a function-separating type electrophotographic photoconductor where an organic or inorganic pigment serves as a charge generating material.

In the photoconductors according to the present invention, at least one [2,2]paracyclophane compound of formula (I) is contained in the photoconductive layers 2, 2a, 2b, 2c, 2d and 2e. The [2,2]paracyclophane compounds can be employed in different ways, for example, as shown in FIGS. 4 through 9.

Figure 4:
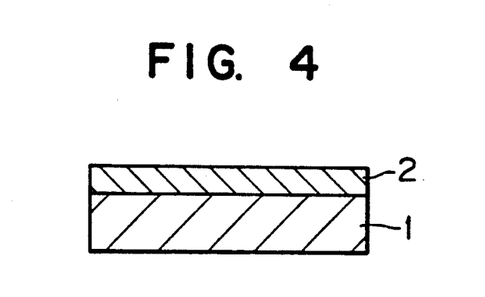
FIG. 4 is a schematic cross-sectional view of a first example of an electrophotographic photoconductor comprising an [2,2]paracyclophane compound according to the present invention.

In the photoconductor as shown in FIG. 4, a photoconductive layer 2 is formed on an electroconductive support 1, which photoconductive layer 2 comprises a [2,2]paracyclophane compound, a sensitizing dye and a binder agent (binder resin). In this photoconductor, the [2,2]paracyclophane compound works as a photoconductive material, through which charge carriers which are necessary for the light decay of the photoconductor are generated and transported. However, the [2,2]paracyclophane compound itself scarcely absorbs light in the visible light range and, therefore, it is necessary to add a sensitizing dye which absorbs light in the visible light range in order to form latent electrostatic images by use of visible light.

Figure 5:
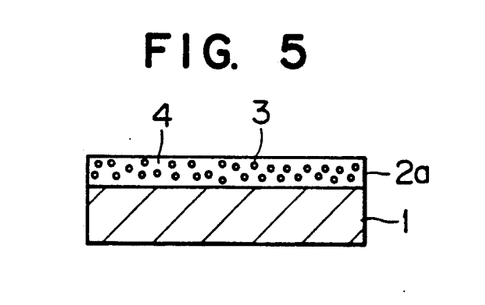
FIG. 5 is a schematic cross-sectional view of a second example of an electrophotographic photoconductor comprising an [2,2]paracyclophane compound according to the present invention.

Referring to FIG. 5, there is shown an enlarged cross-sectional view of another embodiment of an electrophotographic photoconductor according to the present invention. In the figure, reference numeral 1 indicates an electroconductive support. On the electroconductive support 1, there is formed a photoconductive layer 2a comprising a charge generating material 3 dispersed in a charge transporting medium 4 comprising a [2,2]paracyclophane compound and a binder agent. In this embodiment, the [2,2]paracyclophane compound and the binder agent (or a mixture of the binder agent and a plasticizer) constitute the charge transporting medium 4 in combination. The charge generating material 3, which is, for example, an inorganic or organic pigment, generates charge carriers. The charge transporting medium 4 accepts the charge carriers generated by the charge generating material 3 and transports those charge carriers.

In this electrophotographic photoconductor, it is basically necessary that the light-absorption wavelength regions of the charge generating material 3 and the [2,2]paracyclophane compound not overlap in the visible light range. This is because, in order that the charge generating material 3 produce charge carriers efficiently, it is necessary that light pass through the charge transporting medium 4 and reach the surface of the charge generating material 3. Since the [2,2]paracyclophane compounds of the previously described general formula (I) do not substantially absorb light in the visible range, they can work effectively as charge transporting materials in combination with the charge generating material 3 which absorbs the light in the visible region and generates charge carriers.

Figure 6:
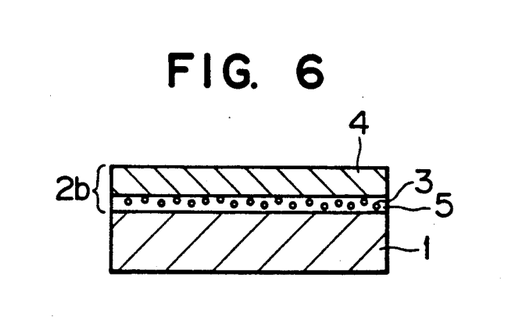
FIG. 6 is a schematic cross-sectional view of a third example of an electrophotographic photoconductor comprising an [2,2]paracyclophane compound according to the present invention.

Referring to FIG. 6, there is shown an enlarged cross-sectional view of a further embodiment of an electrophotographic photoconductor according to the present invention. In the figure, there is formed on an electroconductive support 1 a two-layered photoconductive layer 2b comprising a charge generation layer 5 containing a charge generating material 3, and a charge transport layer 4 containing a [2,2]paracyclophane compound of the previously described formula (I).

In this photoconductor, light which has passed through the charge transport layer 4 reaches the charge generation layer 5, and charge carriers are generated within the charge generation layer 5. The charge carriers which are necessary for the light decay for latent electrostatic image formation are generated by the charge generating material 3, accepted and transported by the charge transport layer 4. In the charge transport layer 4, the [2,2]paracyclophane compound mainly works for transporting charge carriers. The generation and transportation of the charge carriers are performed by the same mechanism as that in the photoconductor shown in FIG. 5.

Figure 7:
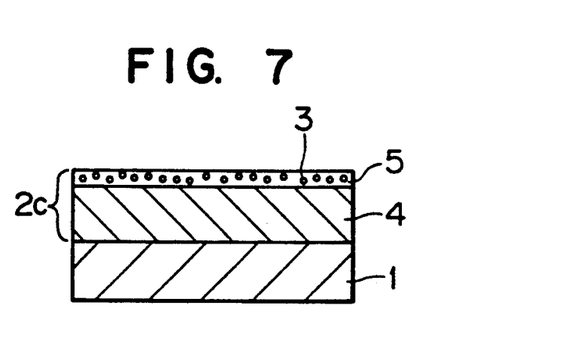
FIG. 7 is a schematic cross-sectional view of a fourth example of an electrophotographic photoconductor comprising an [2,2]paracyclophane compound according to the present invention.

In an electrophotographic photoconductor shown in FIG. 7, a charge generation layer 5 is formed on a charge transport layer 4 containing a [2,2]paracyclophane compound in a photoconductive layer 2c, thus the overlaying order of the charge generation layer 5 and the charge transport layer 4 is reversed as compared with the electrophotographic photoconductor as shown in FIG. 6. The mechanism of the generation and transportation of charge carriers is substantially the same as that of the photoconductor shown in FIG. 6.

Figure 8:
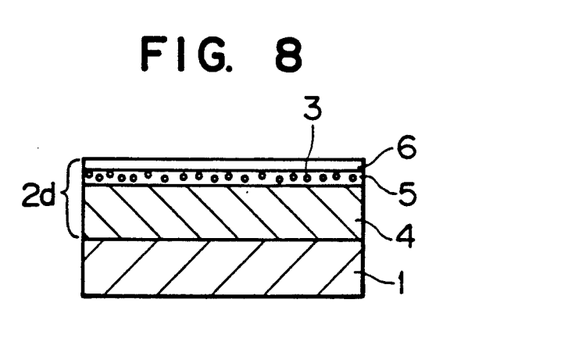
FIG. 8 is a schematic cross-sectional view of a fifth example of an electrophotographic photoconductor comprising an [2,2]paracyclophane compound according to the present invention.

In the above photoconductor, a protective layer 6 may be formed on the charge generation layer 5 as shown in FIG. 8 for protecting the charge generation layer 5.

When the electrophotographic photoconductor according to the present invention as shown in FIG. 4 is prepared, at least one [2,2]paracyclophane compound of the previously described formula (I) is dispersed in a binder resin solution, and a sensitizing dye is then added to the mixture, so that a photoconductive layer coating liquid is prepared. The thus prepared photoconductive layer coating liquid is coated on an electroconductive support 1 and dried, so that a photoconductive layer 2 is formed on the electroconductive support 1.

It is preferably that the thickness of the photoconductive layer 2 be in the range of 3 to 50 μm, more preferably in the range of 5 to 20 μm. It is preferable that the amount of the [2,2]paracyclophane compound contained in the photoconductive layer 2 be in the range or 30 to 70 wt. %, more preferably about 50 wt. %.

It is preferable that the amount of the sensitizing dye contained in the photoconductive layer 2 be in the range of 0.1 to 5 wt. %, more preferably in the range of 0.5 to 3 wt. %.

Specific examples of the sensitizing dye for use in the present invention are: triarylmethane dyes such as Brilliant Green, Victoria Blue B, Methyl Violet, Crystal Violet and Acid Violet 6B; xanthene dyes such as Rhodamine B, Rhodamine 6G, Rhodamine G Extra, Eosin S, Erythrosin, Rose Bengale and Fluoresceine; thiazine dyes such as Methylene Blue; cyanine dyes such as cyanin; and pyrylium dyes such as 2,6-diphenyl-4-(N,N-dimethylaminophenyl)thiapyrylium perchlorate and benzopyrylium salts (Japanese Patent Publication 48-25658).

These sensitizing dyes may be used alone or in combination.

The electrophotographic photoconductor shown in FIG. 5 can be obtained by dispersing finely-divided particles of the charge generating material 3 in a solution in which at least one [2,2]paracyclophane compound for use in the present invention and the binder agent are dissolved, coating the above-prepared dispersion on the electroconductive support 1 and then drying the same to form the photoconductive layer 2a.

It is preferable that the thickness of the photoconductive layer 2a be in the range of 3 to 50 μm, more preferably in the range of 5 to 20 μm. It is preferable that the amount of the [2,2]paracyclophane compound contained in the photoconductive layer 2a be in the range of 10 to 95 wt. %, more preferably in the range of 30 to 90 wt. %.

It is preferable that the amount of the charge generating material 3 contained in the photoconductive layer 2a be in the range of 0.1 to 50 wt. %, more preferably in the range of 1 to 20 wt. %.

Specific examples of the charge generating material 3 for use in the present invention are as follows: inorganic pigments such as selenium, selenium-tellurium, cadmium sulfide, cadmium sulfide-selenium and α-silicone; and organic pigments, such as C.I. Pigment Blue 25 (C.I. 21180), C.I. Pigment Red 41 (C.I. 21200), C.I. Acid Red 52 (C.I. 45100), and C.I. Basic Red 3 (C.I. 45210); an azo pigment having a carbazole skeleton (Japanese Laid-Open Patent Application 53-95033), an azo pigment having a distyryl benzene skeleton (Japanese Laid-Open Patent Application 53-133445), an azo pigment having a triphenylamine skeleton (Japanese Laid-Open Patent Application 53-132347), an azo pigment having a dibenzothiophene skeleton (Japanese Laid-Open Patent Application 54-21728), an azo pigment having an oxadiazole skeleton (Japanese Laid-Open Patent Application 54-12742), an azo pigment having a fluorenone skeleton (Japanese Laid-Open Patent Application 54-22834), an azo pigment having a bisstilbene skeleton (Japanese Laid-Open Patent Application 54-17733), an azo pigment having a distyryl oxadiazole skeleton (Japanese Laid-Open Patent Application 54-2129), and an azo pigment having a distyryl carbazole skeleton (Japanese Laid-Open Patent Application 54-14967); a phthalocyanine pigment such as C.I. Pigment Blue 16 (C.I. 74100); indigo pigments such as C.I. Vat Brown 5 (C.I. 73410) and C.I. Vat Dye (C.I. 73030); and perylene pigments such as Algol Scarlet B and Indanthrene Scarlet R (made by Bayer Co., Ltd.). These charge generating materials may be used alone or in combination.

The electrophotographic photoconductor shown in FIG. 6 can be obtained as follows:

The charge generating material is vacuum-deposited on the electroconductive support 1, or the dispersion in which finely-divided particles of the charge generating material 3 are dispersed in an appropriate solvent together with the binder agent when necessary is coated on the electroconductive support 1 and dried, so that the charge generation layer 5 is formed. When necessary, the charge generation layer 5 is subjected to buffing to adjust the thickness thereof. On the thus formed charge generation layer 5, the coating solution in which at least one [2,2]paracyclophane compound and the binder agent are dissolved is coated and dried, so that the charge transport layer 4 is formed. In the charge generation layer 5, the same charge generating material as employed in the above-mentioned photoconductive layer 2a can be used.

The thickness of the charge generation layer 5 is 5 μm or less, more preferably 2 μm or less. It is preferable that the thickness of the charge transport layer 4 be in the range of 3 to 50 μm, more preferably in the range of 5 to 20 μm. When the charge generation layer 5 is obtained by coating the dispersion in which finely-divided particles of the charge generating material 3 are dispersed in an appropriate solvent together with the binder agent, it is preferable that the amount of finely-divided particles of the charge generating material 3 contained in the charge generation layer 5 be in the range of 10 to 95 wt. %, more preferably in the range of about 50 to 90 wt. %. It is preferable that the amount of the [2,2]paracyclophane compound contained in the charge transport layer 4 be in the range of 10 to 95 wt. %, more preferably in the range of 30 to 90 wt. %.

The electrophotographic photoconductor shown in FIG. 7 can be obtained as follows:

The coating solution in which the [2,2]paracyclophane compound and the binder agent are dissolved is coated on the electroconductive support 1 and dried to form the charge transport layer 4. On the thus formed charge transport layer 4, the dispersion prepared by dispersing finely-divided particles of the charge generating material 3 in the solvent, in which the binder agent is dissolved when necessary, is coated by spray coating and dried to form the charge generation layer 5 on the charge transport layer 4. The amount ratio of components contained in the charge generation layer and charge transport layer is the same as previously described in FIG. 6.

The electrophotographic photoconductor shown in FIG. 8 can be obtained by forming a protective layer 6 on the charge generation layer 5 as obtained in FIG. 7 by spray-coating of an appropriate resin solution. As the resins employed in the protective layer 6, the binder agents to be described later can be used.

Figure 9:
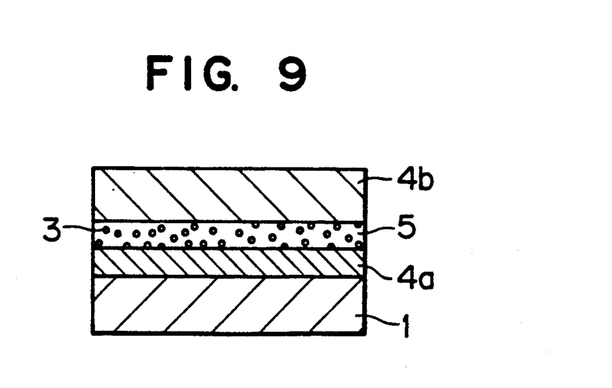
FIG. 9 is a schematic cross-sectional view of a sixth example of an electrophotographic photoconductor comprising an [2,2]paracyclophane compound according to the present invention.

An electrophotographic photoconductor with a structure as shown in FIG. 9 may also be employed in the present invention, which can be obtained by forming a charge transport layer 4a, a charge generation layer 5, and a charge transport layer 4b successively in that order on an electroconductive support 1, in which either the charge transport layer 4a or the charge transport layer 4b comprises at least one [2,2]paracyclophane compound and the other charge transport layer comprises a Lewis acid type charge transporting material, for example, fluorenone compounds such as trichlorofluorenone and quinone derivatives.

Specific examples of the electroconductive support for the electrophotographic photoconductor according to the present invention include a metallic plate or foil made of aluminum, a plastic film on which a metal such as aluminum is deposited, and a sheet of paper which has been treated so as to be electroconductive.

Specific examples of the binder agent for use in the present invention are condensation resins such as polyamide, polyurethane, polyester, epoxy resin, pol ketone and polycarbonate; and vinyl copolymers such as polyvinylketone, polystyrene, poly-N-vinylcarbazole and polyacrylamide. All the resins having insulating properties and adhesive force can be employed. Some plasticizers may be added to the above-mentioned binder agent, when necessary. Examples of the plasticizer for use in the present invention are halogenated paraffin, polybiphenyl chloride, dimethylnaphthalene and dibutyl phthalate.

Furthermore, in the electrophotographic photoconductors according to the present invention, an adhesive layer or barrier layer may be interposed between the electroconductive support and the photoconductive layer when necessary. Examples of the material for use in the adhesive layer or barrier layer are polyamide, nitrocellulose and aluminum oxide. It is preferable that the thickness of the adhesive layer or barrier layer be 1 μm or less.

When copying is performed by use of the photoconductors according to the present invention, the surface of the photoconductor is charged uniformly in the dark to a predetermined polarity. The uniformly charged photoconductor is exposed to a light image so that a latent electrostatic image is formed on the photoconductor. The thus formed latent electrostatic image is developed by a developer to a visible image, and when necessary, the developed image can be transferred to a sheet of paper. The electrophotographic photoconductors according to the present invention have the advantages in that the photosensitivity is high and the flexibility is improved.

Other features of this invention will become apparent in the course of the following description of exemplary embodiments, which are given for illustration of the invention and are not intended to be limiting thereof.

EXAMPLE 1

Preparation of 4-N,N-bis(4-methylphenyl)amino[2,2]paracyclophane (Compound No. 12 in Table 1)

A mixture of 2.40 g (10.7 mmol) of 4-amino[2,2-]paracyclophane, 25.44 g (116.7 mmol) of 4-iodotoluene, 4.45 g of potassium carbonate and 1.20 g of copper powder was refluxed at 211° C. for 16 hours, with stirring in a stream of nitrogen. After the completion of the reflux, the mixture was cooled to room temperature and filtered through Celite. The filtrate was extracted with toluene, washed with water, dried over magnesium sulfate, and further concentrated under reduced pressure. Thus, a brown-red oil-like product was obtained. The thus obtained product was isolated from the reaction mixture by column chromatography using a silica gel and a mixed solvent of n-hexane and toluene serving as a developing solvent, and recrystallized from ethanol, so that 0.47 g of 4-N,N-bis(4-methylphenyl)amino[2,2]paracyclophane was obtained as colorless needles in a 10.8% yield. The melting point was 140.0° to 141.0° C.

The results of the elemental analysis of the thus obtained product were as follows:

|  | % C | % H | % N |
|---|---|---|---|
| Calculated | 89.29 | 7.24 | 3.47 |
| Found | 89.16 | 7.33 | 3.20 |

The above calculation was based on the formula for 4-N,N-bis(4-methylphenyl)amino[2,2]paracyclophane of $C_{30}H_{29}N$.

Figure 1:
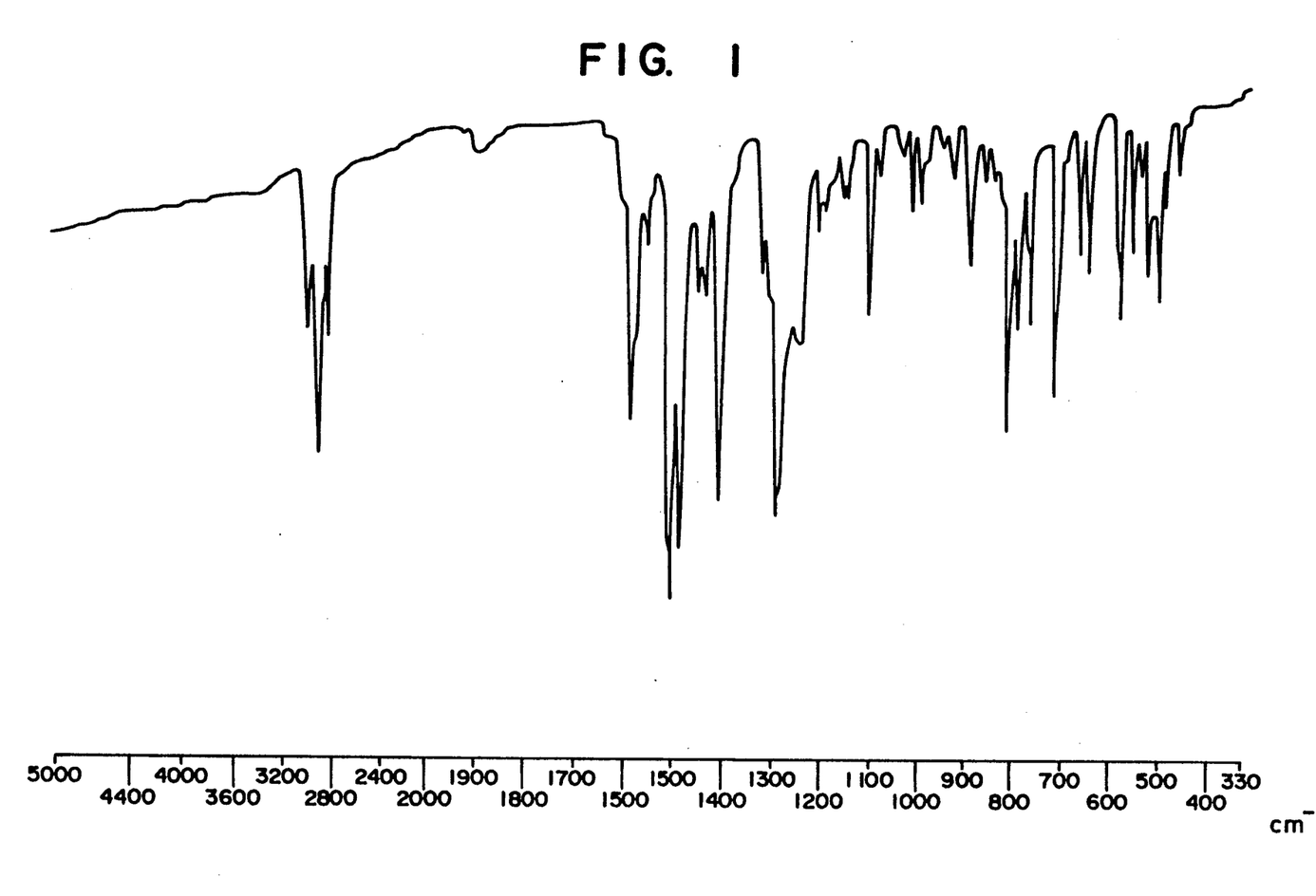
FIG. 1 is an IR spectrum of an [2,2]paracyclophane compound according to the present invention.

FIG. 1 shows an infrared spectrum of 4-N,N-bis(4-methylphenyl)amino[2,2]paracyclophane, taken by use of a KBr tablet.

EXAMPLE 2

Preparation of 4-N,N-bis(4-phenyl)amino[2,2]paracyclophane (Compound No. 10 in Table 1)

In the same manner as in Example 1, 4-N,N-bis(4-phenyl)amino[2,2]paracyclophane was synthesized. The melting point of the product was 158.5° to 159.5° C.

The results of the elemental analysis of the thus obtained product were as follows:

|  | % C | % H | % N |
|---|---|---|---|
| Calculated | 89.56 | 6.71 | 3.73 |
| Found | 89.72 | 6.88 | 3.79 |

Figure 2:
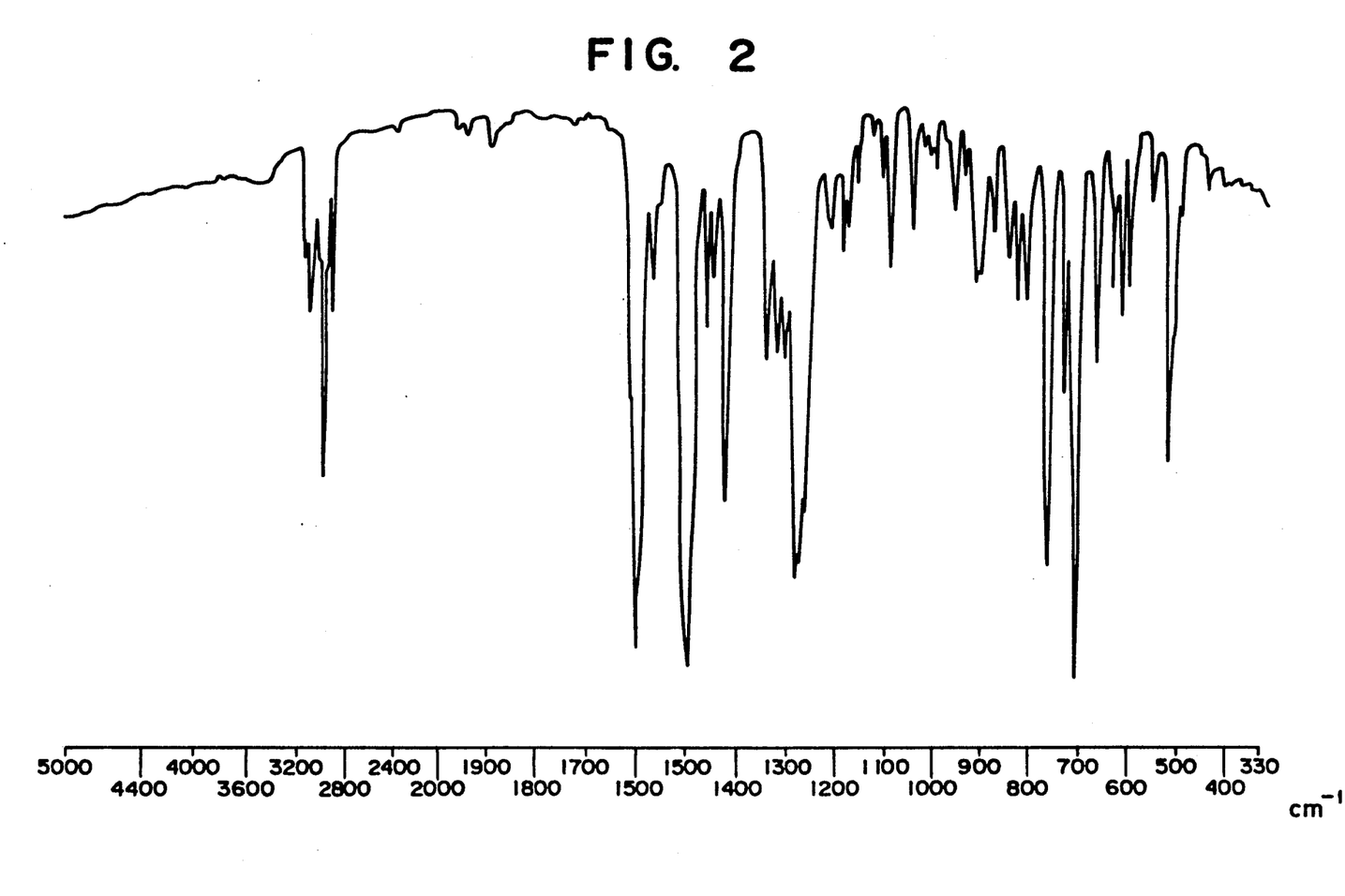
FIG. 2 is an IR spectrum of another [2,2]paracyclophane compound according to the present invention.

FIG. 2 shows an infrared spectrum of 4-N,N-bis(4-phenyl)amino[2,2]paracyclophane, taken by use of a KBr tablet.

EXAMPLE 3

Preparation of 4-N,N-bis(4-methoxyphenyl)amino[2,2]paracyclophane (Compound No. 20 in Table 1)

In the same manner as in Example 1, 4-N,N-bis(4-methoxyphenyl)amino[2,2]paracyclophane was synthesized. The melting point of the product was 145.0° to 146.0° C.

The results of the elemental analysis of the thus obtained product were as follows:

|  | % C | % H | % N |
|---|---|---|---|
| Calculated | 82.72 | 6.71 | 3.22 |
| Found | 82.56 | 6.82 | 3.25 |

Figure 3:
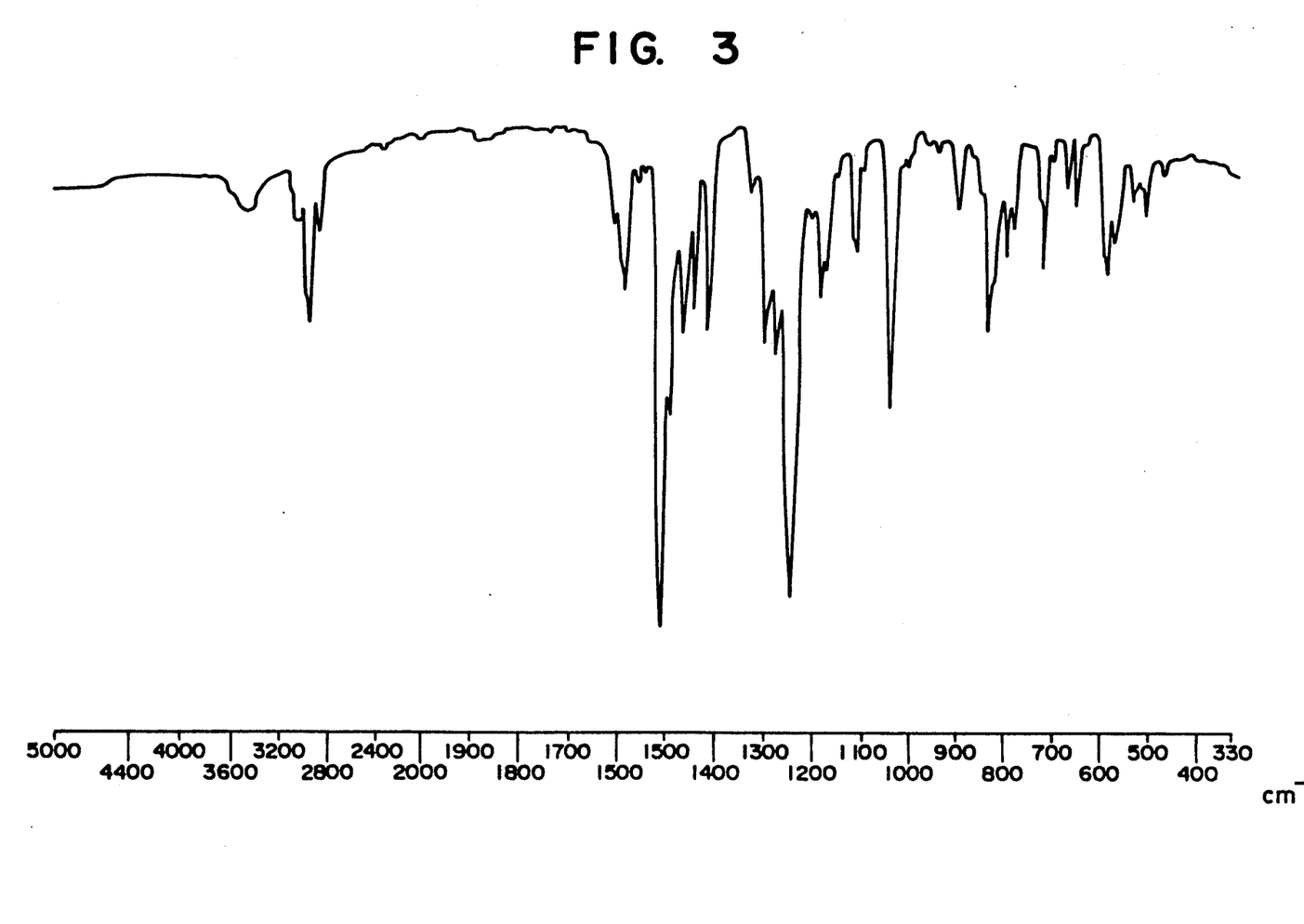
FIG. 3 is an IR spectrum of a further [2,2]paracyclophane compound according to the present invention.

FIG. 3 shows an infrared spectrum of 4-N,N-bis(4-methoxyphenyl)amino[2,2]paracyclophane, taken by use of a KBr tablet.

APPLICATION EXAMPLE 1

76 parts by weight of Diana Blue (C.I. Pigment Blue 25, CI21180) serving as a charge generating material, 1260 parts by weight of a 2% tetrahydrofuran solution of a polyester resin (Trademark "Vylon 200" made by Toyobo Company, Ltd.) and 3700 parts by weight of tetrahydrofuran were dispersed and ground in a ball mill. The thus prepared dispersion was coated on an aluminum surface of an aluminum-deposited polyester film by a doctor blade, and dried at room temperature, so that a charge generation layer having a thickness of about 1 μm was formed on the aluminum-deposited polyester film.

1 part by weight of 4-N,N-bis(4-methylphenyl)amino[2,2]paracyclophane ([2,2]paracyclophane compound No. 12 in Table 1) prepared in the above-mentioned Synthesis Example 1, 1 part by weight of polycarbonate resin (Trademark "Panlite K-1300" made by Teijin Limited.) and 8 parts by weight of tetrahydrofuran were mixed to form a solution. This solution was coated on the above formed charge generation layer by a doctor blade and then dried at 80° C. for 2 minutes and then at 120° C. for 5 minutes, so that a charge transport layer having a thickness of about 20 μm was formed on the charge generation layer. Thus a two-layered type electrophotographic photoconductor No. 1 according to the present invention was prepared.

APPLICATION EXAMPLES 2 to 23

The procedure for Application Example 1 was repeated except that Diane Blue serving as a charge generating material and the [2,2]paracyclophane compound No. 12 serving as a charge transporting material employed in Application Example 1 were replaced by the respective charge generating materials and charge transporting materials listed in the following Table 2, whereby two-layered type electrophotographic photoconductors No. 2 to No. 25 were prepared.

TABLE 2

| Photo-Conductor No. | Charge Generating Material | (2,2)Paracyclophane Compound No. |
|---|---|---|
| 1 | Bisazo compound with two 2-hydroxy-3-phenylcarbamoyl-naphthalene groups linked via azo bonds to a 3,3'-dimethoxy-biphenyl core | 12 |
| 2 | Bisazo compound with two 2-hydroxy-3-phenylcarbamoyl-naphthalene groups linked via azo bonds to a 3,3'-dichloro-biphenyl core | 12 |
| 3 | Bisazo compound with two 2-hydroxy-3-(2,4-dimethylphenylcarbamoyl)-naphthalene groups linked via azo bonds to a distyrylbenzene-type core (hereinafter referred to as P-1) | 12 |

TABLE 2-continued

| Photo-conductor No. | Charge Generating Material | (2,2)Paracyclo-phane Compound No. |
|---|---|---|
| 4 | (structure: bis-azo compound with 1,3,4-oxadiazole central unit linked via two p-phenylene-azo groups to 2-hydroxy-3-(phenylcarbamoyl)naphthalene units) | 12 |
| 5 | (structure: bis-azo compound with 9-fluorenone central unit linked via two azo groups to 2-hydroxy-3-(2-chlorophenylcarbamoyl)naphthalene units) (hereinafter referred to as P-2) | 12 |

TABLE 2-continued

| Photo-Conductor No. | Charge Generating Material | (2,2)Paracyclophane Compound No. |
|---|---|---|
| 6 |  | 12 |
| 7 | β-type Copper Phthalocyanine | 12 |
| 8 |  | 10 |

TABLE 2-continued

| Photo-Conductor No. | Charge Generating Material | (2,2)Paracyclophane Compound No. |
|---|---|---|
| 9 | ![structure: bisazo compound with naphthol-CONH-phenyl groups and dichlorobiphenyl core] | 10 |
| 10 | P-1 | 10 |
| 11 | P-2 | 10 |
| 12 | P-1 | 20 |
| 13 | P-2 | 20 |
| 14 | P-1 | 3 |
| 15 | P-2 | 3 |
| 16 | P-1 | 25 |
| 17 | P-2 | 25 |
| 18 | P-1 | 29 |
| 19 | P-2 | 29 |
| 20 | P-1 | 11 |
| 21 | P-2 | 11 |
| 22 | P-1 | 7 |
| 23 | P-2 | 7 |

APPLICATION EXAMPLE 24

Selenium was vacuum-deposited on an aluminum plate having a thickness of about 300 μm, so that a charge generation layer having a thickness of about 1 μm was formed on the aluminum plate.

2 parts by weight of [2,2]paracyclophane compound No. 10 in Table 1, 3 parts by weight of polyester resin (Trademark "Polyester Adhesive 49000" made by Du Pont de Nemours, E.I. & Co.) and 45 parts by weight of tetrahydrofuran were mixed to form a solution. This solution was coated on the above formed charge generation layer by a doctor blade, dried at room temperature, and then dried under reduced pressure, so that a charge transport layer having a thickness of about 10 μm was formed on the charge generation layer. Thus, a two-layered type electrophotographic photoconductor No. 24 was prepared.

APPLICATION EXAMPLE 25

A perylene pigment having the following formula was vacuum-deposited on an aluminum plate having a thickness of about 300 μm, so that a charge generation layer having a thickness of about 0.6 μm was formed on the aluminum plate;

2 parts by weight of [2,2]paracyclophane compound No. 10 in Table 1, 3 parts by weight of polyester resin (Trademark "Polyester Adhesive 49000" made by Du Pont de Nemours, E.I. & Co.) and 45 parts by weight of tetrahydrofuran were mixed to form a solution. This solution was coated on the above formed charge generation layer by a doctor blade, dried at room temperature, and then dried under reduced pressure, so that a charge transport layer having a thickness of about 10 μm was formed on the charge generation layer. Thus a two-layered type electrophotographic photoconductor No. 25 was prepared.

APPLICATION EXAMPLE 26

A mixture of 1 part by weight of the same Diane Blue as employed in Example 1 and 158 parts by weight of tetrahydrofuran was dispersed and ground in a ball mill to form a dispersion. To the thus formed dispersion, 12 parts by weight of [2,2]paracyclophane compound No. 10 in Table 1 and 18 parts by weight of polyester resin (Trademark "Polyester Adhesive 49000" made by Du Pont de Nemours, E.I. & Co.) were added to form a solution. This solution was coated on an aluminum-deposited polyester film by a doctor blade, and dried at 100° C. for 30 minutes, so that a photoconductive layer having a thickness of about 16 μm was formed on the elecroconductive support. Thus, an electrophotographic photoconductor No. 26 was prepared.

APPLICATION EXAMPLE 27

1 part by weight of [2,2]paracyclophane compound No. 12 in Table 1, 1 part by weight of polycarbonate resin (Trademark "Panlite K-1300" made by Teijin Limited.) and 8 parts by weight of tetrahydrofuran were mixed to form a solution. This solution was coated on an aluminum-deposited polyester film by a doctor blade and then dried at 80° C. for 2 minutes and then at 120° C. for 5 minutes, so that a charge transport layer having a thickness of about 20 μm was formed on the aluminum-deposited polyester film.

A mixture of 13.5 parts by weight of bisazo pigment (P-2), 5.4 parts by weight of polyvinyl butyral (Trademark "XYHL" made by Union Carbide Japan K.K.), 680 parts by weight of tetrahydrofuran and 1020 parts by weight of ethyl cellosolve was dispersed and ground in a ball mill. To this dispersion, 1700 parts by weight of ethyl cellosolve was further added to form a solution. This solution was coated on the above formed charge transport layer by spray coating and dried at 100° C. for 10 minutes, so that a charge generation layer having a thickness of about 0.2 μm was formed on the charge transport layer.

A mixed solution of methanol and n-butanol containing a polyamide resin (Trademark "CM-8000" made by Toray Silicone Co., Ltd.) was coated on the above formed charge generation layer by spray coating and dried at 120° C. for 30 minutes, so that a protective layer having a thickness of about 0.5 μm was formed on the charge generation layer. Thus, a two-layered type electrophotographic photoconductor No. 27 was prepared.

Each of the thus prepared electrophotographic photoconductors No. 1 through No. 27 according to the present invention was charged negatively or positively in the dark under application of −6 kV or +6 kV of corona charge for 20 seconds, using a commercially available electrostatic copying sheet testing apparatus ("Paper Analyzer Model SP-428" made by Kawaguchi Electro Works Co., Ltd.). Then, each electrophotographic photoconductor was allowed to stand in the dark for 20 seconds without applying any charge thereto, and the surface potential Vpo (V) of the photoconductor was measured. The photoconductor was then illuminated by a tungsten lamp in such a manner that the illuminance on the illuminated surface of the photoconductor was 4.5 lux, and the exposure $E_{\frac{1}{2}}$(lux.-sec) required to reduce the initial surface potential Vpo (V) to $\frac{1}{2}$ the initial surface potential Vpo (V) was measured. The results are shown in Table 3.

TABLE 3

| Photoconductor No. | Vpo (V) | $E_{\frac{1}{2}}$ (lux · sec) |
|---|---|---|
| 1 | −1110 | 1.79 |
| 2 | −1220 | 1.68 |
| 3 | −1310 | 1.15 |
| 4 | −1014 | 1.85 |
| 5 | −1212 | 1.10 |
| 6 | −1010 | 1.20 |
| 7 | −980 | 2.00 |
| 8 | −1205 | 1.84 |
| 9 | −1250 | 1.75 |
| 10 | −1150 | 1.24 |
| 11 | −1215 | 1.18 |
| 12 | −1063 | 1.14 |
| 13 | −965 | 1.05 |
| 14 | −863 | 2.01 |
| 15 | −654 | 1.92 |
| 16 | −1310 | 1.16 |
| 17 | −1292 | 1.04 |
| 18 | −1305 | 1.12 |
| 19 | −1224 | 0.98 |
| 20 | −1294 | 1.20 |
| 21 | −1254 | 1.15 |
| 22 | −1415 | 1.50 |
| 23 | −1312 | 1.40 |
| 24 | −956 | 2.11 |
| 25 | −1340 | 3.68 |
| 26 | +1420 | 2.88 |
| 27 | +1298 | 1.15 |

Each of the above-mentioned electrophotographic photoconductors according to the present invention was incorporated in a commercially available electrophotographic copying machine and charged negatively or positively. Then it was exposed to the light through an original to form a latent electrostatic image on the surface of the photoconductor. The thus formed latent electrostatic image was developed by a dry-type developer to a visible image. The thus obtained visible image was transferred to a sheet of plain paper and fixed thereon, so that a clear transferred image was formed. In the case where a wet-type developer was employed, a clear image was formed likewise. The electrophotographic photoconductor according to the present invention comprises a photoconductive layer comprising at least one [2,2]paracyclophane compound serving as a charge transporting material. As a result, the resistance to heat and mechanical shocks of the photoconductor can be improved as well as the photoconductive properties thereof, and further the photoconductor according to the present invention can be manufactured at relatively low cost.

What is claimed is:

1. A [2,2]paracyclophane compound having formula (I):

wherein $R^1$ and $R^2$ independently represent an alkyl group having 1 to 4 carbon atoms, which may have a substituent, or an aryl group which may have a substituent, provided that $R^1$ and $R^2$ may not be a methyl group at the same time.

2. The [2,2]paracyclophane compound as claimed in claim 1, wherein said substituent of said alkyl group represented by $R^1$ or $R^2$ is selected from the group consisting of a phenyl group and an alkyl phenyl group; and said aryl group is selected from the group consisting of a phenyl group a biphenyl group and a phenoxyphenyl group, and said substituent thereof being selected from the group consisting of an alkyl group having 1 to 4 carbon atoms, an alkoxy group having 1 to 4 carbon atoms, and a dialkylamino group.

3. The [2,2]paracyclophane compound as claimed in claim 2, wherein at least one of $R^1$ or $R^2$ is said aryl group.

4. The [2,2]paracyclophane compound as claimed in claim 3, wherein $R^1$ and $R^2$ independently represent said aryl group.

5. The [2,2]paracyclophane compound as claimed in claim 4, wherein the substituents of $R^1$ and $R^2$ are the same.

6. The [2,2]paracyclophane compound as claimed in claim 3, wherein said aryl group represented by $R^1$ or $R^2$ is a phenyl group.

7. The [2,2]paracyclophane compound as claimed in claim 4, wherein said aryl group represented by $R^1$ or $R^2$ is a phenyl group.

8. The [2,2]paracyclophane compound as claimed in claim 5, wherein said aryl group represented by $R^1$ or $R^2$ is a phenyl group.

9. The [2,2]paracyclophane compound as claimed in claim 5, wherein $R^1$ and $R^2$ each represent a phenyl group which may have a substituent selected from the group consisting of an alkyl group having 1 to 4 carbon atoms and an alkoxy group having 1 to 4 carbon atoms.

10. The [2,2]paracyclophane compound as claimed in claim 2, wherein $R^1$ and $R^2$ are the same and selected from the group consisting of an ethyl group and a phenyl group.

11. The [2,2]paracyclophane compound as claimed in claim 2, wherein $R^1$ and $R^2$ independently represent a phenyl or biphenyl group which may have a substituent selected from the group consisting of an alkyl group having 1 to 4 carbon atoms and an alkoxyl group having 1 to 4 carbon atoms.

12. The [2,2]paracyclophane compound as claimed in claim 11, wherein the substituents of $R^1$ and $R^2$ are the same.

13. The [2,2]paracyclophane compound as claimed in claim 12, wherein $R^1$ and $R^2$ each represent a phenyl group which may have a substituent selected from the group consisting of a methyl group and a methoxy group.

14. The [2,2]paracyclophane compound as claimed in claim 13, wherein $R^1$ and $R^2$ each represent an unsubstituted phenyl group.

15. The [2,2]paracyclophane compound as claimed in claim 13, wherein $R^1$ and $R^2$ are a methylphenyl group.

16. The [2,2]paracyclophane compound as claimed in claim 13, wherein $R^1$ and $R^2$ are a methoxyphenyl group.

* * * * *

UNITED STATES PATENT AND TRADEMARK OFFICE
CERTIFICATE OF CORRECTION

PATENT NO. : 5,233,090
DATED : August 3, 1993
INVENTOR(S) : Tomoyuki Shimada, et al It is certified that error appears in the above-indentified patent and that said Letters Patent is hereby corrected as shown below:

Column 9, Line 44, "It is preferably that the thickness" should read --It is preferable that the thickness--

Column 14, Line 6, "Diana Blue" should read --Diane Blue--

Signed and Sealed this

Twenty-fifth Day of October, 1994

Attest:

BRUCE LEHMAN

*Attesting Officer*     *Commissioner of Patents and Trademarks*